United States Patent [19]

Daum et al.

[11] Patent Number: 4,863,954
[45] Date of Patent: Sep. 5, 1989

[54] ACYLOXYTHIOPHENE-CARBOXAMIDE FUNGICIDES

[75] Inventors: Werner Daum, Krefeld; Gerd Hänssler, Leverkusen, both of Fed. Rep. of Germany

[73] Assignee: Bayer Aktiengesellschaft, Leverkusen, Fed. Rep. of Germany

[21] Appl. No.: 194,742

[22] Filed: May 17, 1988

Related U.S. Application Data

[62] Division of Ser. No. 27,755, Mar. 19, 1987, Pat. No. 4,767,757.

[30] Foreign Application Priority Data

Mar. 29, 1986 [DE] Fed. Rep. of Germany ....... 3610711

[51] Int. Cl.⁴ .................... A01N 43/10; C07D 333/38
[52] U.S. Cl. ........................................ 514/445; 549/64
[58] Field of Search .......................... 549/64; 514/445

[56] References Cited

U.S. PATENT DOCUMENTS 4,752,607  6/1988  Daum et al. ........................ 549/64
4,757,085  7/1988  Daum et al. ........................ 549/64

FOREIGN PATENT DOCUMENTS 0095184  8/1981  Japan .
0013702  1/1985  Japan .................................. 549/64

*Primary Examiner*—Mary C. Lee
*Assistant Examiner*—MarySue Howard
*Attorney, Agent, or Firm*—Sprung Horn Kramer & Woods

[57] ABSTRACT

Novel fungicidally active acyloxythiophene-carboxamides of the formula

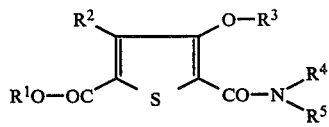

in which
 $R^1$ represents alkyl, alkoxyalkyl, alkylthioalky, fluoroalkyl, cyanoalkyl, alkenyl, alkinyl or cycloalkyl,
 $R^2$ represents alkyl or optionally substituted phenyl,
 $R^3$ represents alkylsulphonyl, halogenoalkylsulphonyl, optionally substituted phenylsulphonyl or the —OC—Q radical, in which
 Q represents alkyl which is optionally identically or differently substituted by halogen, alkoxy, alkylthio, alkylsulphonyl, alkylthioalkoxy, alkoxycarbonyl, phenyl, phenoxy or halogenophenoxy; alkenyl which is optionally identically or differently substituted by halogen, phenyl, halogenophenyl or halogenoalkylphenyl; alkinyl; cycloalkyl; alkoxy which is optionally substituted by halogen or cyano; phenyl which is optionally identically or differently substituted by halogen, alkyl, halogenoalkyl, alkoxy, halogenoalkoxy, alkylthio, halogenoalkylthio, alkylsulphinyl, halogenoalkylsulphinyl, alkylsulphonyl or halogenoalkylsulphonyl; pyridyl; monoalkylamino, the alkyl part being optionally substituted by halogen, cyano, alkoxycarbonyl, dialkylaminocarbonyl, alkanyleneaminocarbonyl or oxaalkanyleneaminocarbonyl; 1-cyanocycloalkylamino; dialkylamino; alkanyleneamino; oxaalkanyleneamino; N-alkyl-N-phenylamino or phenylamino, in which the phenyl radical in each is optionally identically or differently substituted by halogen, alkyl, halogenoalkyl, alkoxy, halogenoalkoxy, alkylthio, halogenoalkylthio, alkylsulphonyl, halogenoalkylsulphonyl, alkanylenedioxy, halogenoalkanylenedioxy or by —O—CHal$_2$—O—CHal$_2$-, or
 $R^4$ represents alkyl, alkoxyalkyl, alkylthioalkyl, cyanoalkyl, fluoroalkyl, alkenyl, alkinyl, cycloalkyl or alkoxy,
 $R^5$ represents hydrogen, alkyl, alkoxyalkyl, alkylthioalkyl, fluoroalkyl, cyanoalkyl, alkenyl, alkinyl or cycloalkyl,
 $R^4$ and $R^5$, together with the adjacent nitrogen atom represent an optionally substituted heterocycle which can be substituted, in the alkylene chain, by further heteroatoms.

14 Claims, No Drawings

ACYLOXYTHIOPHENE-CARBOXAMIDE FUNGICIDES

This is a division of application Ser. No. 027,755, filed Mar. 19, 1987, now U.S. Pat. No. 4,767,757.

The present invention relates to new acyloxythiophene-carboxamides, processes for their preparation, and their use as pesticides, above all as fungicides.

It has already been disclosed that 2,5-bis-(alkoxycarbonyl)-3,4-bis-(acyloxy)-thiophenes and 2,5-bis-(alkoxycarbonyl)-3-alkyl-4-acyloxythiophenes have fungicidal properties (cf. European Patent Specification 32,748 and European Patent Specification 93,384). 2,5-Bis-(isopropoxycarbonyl)-3-methyl-4-(3-methylbenzoyloxy)-thiophene, which was disclosed by T. Wada et al., Proceedings of the 10th Intern. Congress of Plant Protection, Nov. 20-25, 1983, Brighton, Vol. 1, 400–407, should be mentioned particularly here.

New acyloxythiophene-carboxamides of the general formula (I)

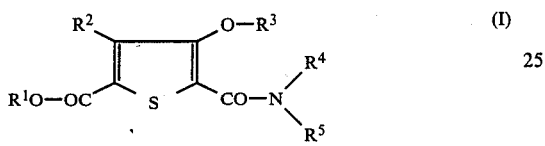

in which
- $R^1$ represents alkyl, alkoxyalkyl, alkylthioalkyl, fluoroalkyl, cyanoalkyl, alkenyl, alkinyl or cycloalkyl,
- $R^2$ represents alkyl or optionally substituted phenyl,
- $R^3$ represents alkylsulphonyl, halogenoalkylsulphonyl, optionally substituted phenylsulphonyl or the —OC—Q radical, in which
- Q represents alkyl which is optionally identically or differently substituted by halogen, alkoxy, alkylthio, alkylsulphonyl, alkylthioalkoxy, alkoxycarbonyl, phenyl, phenoxy or halogenophenoxy; alkenyl which is optionally identically or differently substituted by halogen, phenyl, halogenophenyl or halogenoalkylphenyl; alkinyl; cycloalkyl; alkoxy which is optionally substituted by halogen or cyano; phenyl which is optionally identically or differently substituted by halogen, alkyl, halogenoalkyl, alkoxy, halogenoalkoxy, alkylthio, halogenoalkylthio, alkylsulphinyl, halogenoalkylsulphinyl, alkylsulphonyl or halogenoalkylsulphonyl; pyridyl; monoalkylamino, the alkyl part being optionally substituted by halogen, cyano, alkoxycarbonyl, dialkylaminocarbonyl, alkanyleneaminocarbonyl or oxaalkanyleneaminocarbonyl; 1-cyanocycloalkylamino; dialkylamino; alkanyleneamino; oxaalkanyleneamino; N-alkyl-N-phenylamino or phenylamino, in which the phenyl radical in each case is optionally identically or differently substituted by halogen, alkyl, halogenoalkyl, alkoxy, halogenoalkoxy, alkylthio, halogenoalkylthio, alkylsulphonyl, halogenoalkylsulphonyl, alkanylenedioxy, halogenoalkanylenedioxy or by —O—CHal$_2$—O—CHal$_2$—, or alkoxycarbonylamino,
- $R^4$ represents alkyl, alkoxyalkyl, alkylthioalkyl, cyanoalkyl, fluoroalkyl, alkenyl, alkinyl, cycloalkyl or alkoxy,
- $R^5$ represents hydrogen, alkyl, alkoxyalkyl, alkylthioalkyl, fluoroalkyl, cyanoalkyl, alkenyl, alkinyl or cycloalkyl,
- $R^4$ and $R^5$, together with the adjacent nitrogen atom, represent an optionally substituted heterocycle which can be substituted, in the alkylene chain, by further heteroatoms, have been found.

It has furthermore been found that the new acyloxythiophene-carboxamides of the formula (I)

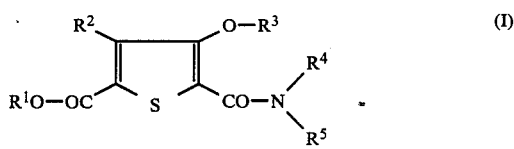

in which
- $R^1$ represents alkyl, alkoxyalkyl, alkylthioalkyl, fluoroalkyl, cyanoalkyl, alkenyl, alkinyl or cycloalkyl,
- $R^2$ represents alkyl or optionally substituted phenyl,
- $R^3$ represents alkylsulphonyl, halogenoalkylsulphonyl, optionally substituted phenylsulphonyl or the —OC—Q radical, in which
- Q represents alkyl which is optionally identically or differently substituted by halogen, alkoxy, alkylthio, alkylsulphonyl, alkylthioalkoxy, alkoxycarbonyl, phenyl, phenoxy or halogenophenoxy; alkenyl which is optionally identically or differently substituted by halogen, phenyl, halogenophenyl or halogenoalkylphenyl; alkinyl; cycloalkyl; alkoxy which is optionally substituted by halogen or cyano; phenyl which is optionally identically or differently substituted by halogen, alkyl, halogenoalkyl, alkoxy, halogenoalkoxy, alkylthio, halogenoalkylthio, alkylsulphinyl, halogenoalkylsulphinyl, alkylsulphonyl or halogenoalkylsulphonyl; pyridyl; monoalkylamino, the alkyl part being optionally substituted by halogen, cyano, alkoxycarbonyl, dialkylaminocarbonyl, alkanyleneaminocarbonyl or oxaalkanyleneaminocarbonyl; 1-cyanocycloalkylamino; dialkylamino; alkanyleneamino; oxaalkanyleneamino; N-alkyl-N-phenylamino or phenylamino, in which the phenyl radical in each is optionally identically or differently substituted by halogen, alkyl, halogenealkyl, alkoxy, halogenoalkoxy, alkylthio, halogenoalkylthio, alkylsulphonyl, halogenoalkylsulphonyl, alkanylenedioxy, halogenoalkanylenedioxy or by —O—CHal$_2$—O—CHal$_2$—, or represents alkoxycarbonylamino,
- $R^4$ represents alkyl, alkoxyalkyl, alkylthioalkyl, cyanoalkyl, fluoroalkyl, alkenyl, alkinyl, cycloalkyl or alkoxy,
- $R^5$ represents hydrogen, alkyl, alkoxyalkyl, alkylthioalkyl, fluoroalkyl, cyanoalkyl, alkenyl, alkinyl or cycloalkyl,
- $R^4$ and $R^5$, together with the adjacent nitrogen atom represent an optionally substituted heterocycle which can be substituted, in the alkylene chain, by further heteroatoms, are obtained when (a) a 4-hydroxythiophene-5-carboxamide of the formula (II)

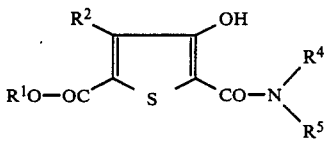

in which

R$^1$, R$^2$, R$^4$ and R$^5$ have the abovementioned meanings, is reacted with an acylating agent of the formula (III)

$$X—R^3 \quad \text{(III)}$$

in which

R$^3$ has the abovementioned meaning, and

X represents a leaving group, such as, for example, halogen, or (b) compounds of the formula (II) are reacted with an isocyanate of the formula (IV)

$$OCN—Y \quad \text{(IV)}$$

in which

Y represents alkyl which is optionally identically or differently substituted by halogen, cyano, alkoxycarbonyl, dialkylaminocarbonyl, alkanyleneaminocarbonyl, or oxaalkanyleneaminocarbonyl; 1-cyanocycloalkyl, alkoxycarbonyl or phenyl which is optionally identically or differently substituted by halogen, alkyl, halogenoalkyl, alkoxy, halogenoalkoxy, alkylthio, halogenoalkylthio, alkylsulphonyl, halogenoalkylsulphonyl, alkanylenedioxy, halogenoalkanylenedioxy or by the radical —OCHal$_2$—O—CHal$_2$—, or when (c) In the case where R$^3$ is a substituted aminocarbonyl radical, a hydroxy-thiophene-carboxamide of the formula (II) is reacted, in a first stage, with phosgene in the presence of a tertiary organic base, and the formed 4-(chlorocarbonyloxy)-thiophene-5-carboxamide derivative of the formula (V)

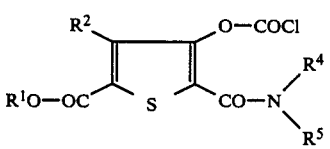

in which

R$^1$, R$^2$, R$^4$ and R$^5$ have the abovementioned meanings, is reacted with an amine of the formula (VI)

$$HN\begin{smallmatrix}Y\\Z\end{smallmatrix} \quad \text{(VI)}$$

in which

Y has the abovementioned meaning, and

Z represents hydrogen or alkyl, or

Y and Z together represent alkanylene or oxyalkanylene, if appropriate in the presence of a solvent or diluent and if appropriate in the presence of a tertiary organic base.

It has furthermore been found that the new acyloxythiophene-carboxamides of the formula (I) are biologically active.

Surprisingly, the acyloxythiophene-carboxamides of the formula (I) display a better effectiveness against pests than the compounds, known from the prior art, of the same mode of action or constitutionally similar compounds.

The acyloxythiophene-carboxamides according to the invention are generally defined by the formula (I). Preferred compounds of the formula (I) are those in which R$^1$ represents alkyl having 1 to 5 carbon atoms, alkoxyalkyl, or alkylthioalkyl having 1 to 5 carbon atoms in each of the alkyl parts, fluoroalkyl having 1 to 5 carbon atoms and 1 to 5 fluorine atoms, cyanoalkyl having 1 to 5 carbon atoms in the alkyl part, alkenyl having 3 or 4 carbon atoms, alkinyl having 3 to 5 carbon atoms, or cycloalkyl having 4 to 6 carbon atoms, R$^2$ represents alkyl having 1 to 4 carbon atoms, or optionally mono- to pentasubstituted phenyl, the substituents being identical or different and suitable substituents being alkyl having 1 to 4 carbon atoms, alkoxy or alkylthio each having 1 to 4 carbon atoms, halogen, nitro, halogenoalkyl, halogenoalkoxy or halogenoalkylthio each having 1 to 4 carbon atoms and 1 to 5 identical or different halogen atoms, R$^3$ represents alkylsulphonyl having 1 to 4 carbon atoms, halogenoalkylsulphonyl having 1 to 4 carbon atoms and 1 to 4 identical or different halogen atoms, phenylsulphonyl, where the phenyl radical can be mono- to pentasubstituted, identically or differently, by halogen, alkyl having 1 to 4 carbon atoms or by nitro, or represents the radical —OC—Q, in which Q represents alkyl having 1 to 4 carbon atoms and which can be optionally substituted by up to 4 identical or different halogen atoms, alkoxy, alkylthio, alkylsulphonyl or alkoxycarbonyl each having up to 4 carbon atoms, alkylthioalkoxy having up to 2 carbon atoms in each alkyl unit, phenyl, phenoxy, or halogenophenoxy having up to 3 identical or different halogen atoms; alkenyl having 2 to 4 carbon atoms and which can optionally be substituted by 1 to 4 identical or different halogen atoms, phenyl, halogenophenyl having 1 to 3 identical or different halogen atoms or halogenolalkylphenyl having 1 to 3 identical or different halogen atoms and 1 or 2 carbon atoms in the halogenoalkyl radical; alkinyl having up to 3 carbon atoms; cycloalkyl having 3 to 6 carbon atoms; alkoxy, having 1 to 4 carbon atoms, which can be optionally substituted by up to 3 identical or different halogen atoms, or cyano; phenyl which can be optionally mono- to trisubstituted, identically or differently, by identical or different halogen atoms, alkyl having 1 to 4 carbon atoms, halogenoalkyl having 1 or 2 carbon atoms and 1 to 3 identical or different halogen atoms, alkoxy having 1 or 2 carbon atoms, halogenoalkoxy having 1 or 2 carbon atoms and 1 to 3 identical or different halogen atoms, alkylthio having 1 or 2 carbon atoms, halogenoalkylthio having 1 or 2 carbon atoms and 1 to 3 identical or different halogen atoms, alkylsulphinyl having 1 or 2 carbon atoms, halogenoalkylsulphinyl having 1 or 2 carbon atoms and 1 to 3 identical or different halogen atoms, alkylsulphonyl having 1 or 2 carbon atoms, or halogenoalkylsulphonyl having 1 or 2 carbon atoms and 1 to 3 identical or different halogen atoms; pyridyl; alkylamino, having 1 to 6 carbon atoms, which can optionally be substituted in the alkyl group by 1 to 4 identical or different halogen atoms, cyano, alkoxycarbonyl having 1 to 6 carbon atoms in the alkoxy group, dialkylaminocarbonyl having 1 to 3 carbon atoms in each alkyl part, alkanyleneaminocarbonyl or oxaalkanyleneaminocarbonyl each having up to 6 carbon atoms in the alkanylene part; 1-cyanocycloalkylamino having 5 or 6 carbon atoms in the cycloalkyl part; dialkylamino having 1 to 3 carbon atoms in each alkyl part, alkanyleneamino and oxaalkanyleneamino each having up to 6 carbon atoms, N-alkyl-N-phenylamino having 1 to 3 carbon atoms in the alkyl part, or phenylamino, where the phenyl radical in each case can be mono- to trisubstituted, identically or differently, by identical or different halogen atoms, by alkyl, alkoxy, alkylthio or alkylsulphonyl each having 1 or 2 carbon atoms, halogenoalkyl, halogenoalkoxy, halogenoalkylthio or halogenoalkylsulphonyl each having 1 or 2 carbon atoms and 1 to 3 identical or different halogen atoms, alkanylenedioxy having 1 or 2 carbon atoms, halogenoalkanylenedioxy having 1 or 2 carbon atoms and up to 4 halogen atoms, or by the radical —O—CHal$_2$—O—CHal$_2$—, or represents alkoxycarbonylamino having 1 to 8 carbon atoms in the alkyl part, $R^4$ represents alkyl having 1 or 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl each having 3 to 5 carbon atoms, cycloalkyl having 3 to 6 carbon atoms, or alkoxy having 1 to 5 carbon atoms, $R^5$ represents hydrogen, alkyl having 1 to 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl having 3 to 5 carbon atoms, or cycloalkyl having 6 carbon atoms, or $R^4$ and $R^5$, together with the nitrogen atom, represent a 5-, 6- or 7-membered heterocyclic ring which can contain aza, oxa or thiaelements and which can be identically or differently substituted by alkyl groups having 1 to 4 carbon atoms.

Halogen denotes fluorine, chlorine, bromine and iodine, preferably fluorine and chlorine, in all the above definitions, unless otherwise defined.

Particularly preferred compounds of the formula (() are those in which $R^1$ represents methyl, ethyl, n- or iso-propyl, 2,2-dimethylpropyl, 2-methoxyethyl, 2-ethoxyethyl, 2-methylthioethyl, 2-ethylthioethyl, 2,2,2-trifluoroethyl, cyanomethyl, cyanoethyl, allyl, methallyl, 2-propinyl, 1,1-dimethyl-2-propinyl, cyclopentyl or cyclohexyl, $R^2$ represents methyl, ethyl, n-propyl, isopropyl, n-butyl, sec-butyl, iso-butyl or tert.-butyl, phenyl or phenyl which is mono- to trisubstituted, identically or differently, by halogen, $R^3$ represents methanesulphonyl, chloromethanesulphonyl, phenylsulphonyl, 2-, 3- and 4-chlorophenylsulphonyl, 3,4-dichlorophenylsulphonyl, 2- and 4-methylphenylsulphonyl, 3-chloro-4-methylphenylsulphonyl, 2-, 3- and 4-nitrophenylsulphonyl, 2-chloro-5-nitrophenylsulphonyl, 2,4,5-trifluoro-3-nitrophenylsulphonyl, 2-methyl-5-nitrophenylsulphonyl or the —OC—Q radical, where Q represents methyl, ethyl, isopropyl, butyl, dichloromethyl, trichloromethyl, trifluoromethyl, 1-bromo-1-methylethyl, methoxymethyl, butoxymethyl, 2-butylthioethyl, propylsulphonylmethyl, methoxycarbonylethyl, butoxycarbonylethyl, methylthioethoxymethyl, benzyl, phenoxymethyl, 1-phenoxy-ethyl, 1-(4-chlorophenoxy)-ethyl, 2,4-dichloro-phenoxymethyl; vinyl, propen-1-yl, 2-chlorovinyl, 2-(phenyl)vinyl, 2-(4-chlorophenyl)-vinyl, 2-(4-chlorophenyl)-2-chlorovinyl, 2-(2-trifluoromethylphenyl)-vinyl, ethinyl, 2-methylethinyl, cyclopropyl, cyclobutyl, cyclopentyl, cyclohexyl, methoxy, isopropoxy, butoxy, 2-chloroethoxy, 2,2,2-trichloroethoxy, 2,2,2-trifluoroethoxy, 2-cyanoethoxy; phenyl, 2-, 3- or 4-chlorophenyl, 2-bromophenyl, 4-fluorophenyl, 2-, 3- or 4-methylphenyl, 4-tert.butylphenyl, 2-, 3- or 4-trifluoromethylphenyl, 3-chloro-4-trifluoromethylphenyl, 4-methoxyphenyl, 3-trifluoromethoxyphenyl, 3-chloro-4-trifluoromethoxyphenyl, 4-chlorodifluoromethoxyphenyl, 4-ethylthiophenyl, 4-trifluoromethylthiophenyl, 4-ethylsulphinylphenyl, 4-trifluoromethylsulphinylphenyl, 4-methylsulphonylphenyl, 4-trifluoromethylsulphonylphenyl; 2-, 3- or 4-pyridyl; methylamino, butylamino, hexylamino, 2,2,2-trifluoroethylamino, 1-trifluoromethyl-ethylamino, 6-chlorohexylamino, 2-cyanoethylamino, 1-cyano-1-methylethylamino, 1-cyano-1-methylpropylamino, 1-cyano-1-ethylpropylamino, 1-cyano-cyclopent-1-ylamino, 1-cyanocyclohex-1-ylamino, 3-cyanopropylamino, 5-cyanopentylamino, 6-cyanohexylamino, methoxycarbonylmethylamino, ethoxycarbonylmethylamino, butylcarbonylethylamino, isobutoxycarbonylethylamino, 1-methoxycarbonyl-1-methyl-ethylamino, 1-propoxycarbonyl-1-methylethylamino, 1-ethoxycarbonyl-1-ethyl-ethylamino, 1-isobutoxycarbonyl-1-ethyl-ethylamino, methoxycarbonyl-propylamino, methoxycarbonylpentylamino, isopropoxycarbonyl-pentylamino, sec.-butyloxycarbonyl-pentylamino, 2-ethoxycarbonyl-2-ethyl-butylamino, butoxycarbonylpentylamino, 5-(2,2-dimethylpropyloxycarbonyl)pentylamino, N-morpholinocarbonylmethylamino, 1-(N,N-diethylaminocarbonyl)-ethylamino, 2-(N-pyrrolidinocarbonyl)-ethylamino, 3-(N-piperidinocarbonyl)-propylamino, 5-(N,N-dimethylaminocarbonyl)-pentylamino; 1-cyanocyclohex-1-ylamino, dimethylamino, diethylamino, pyrrolidino, piperidino, 3,5-dimethylmorpholino, N-methyl-N-phenylamino, phenylamino, 2-chlorophenylamino, 2,4,5-trichlorophenylamino, 4-fluorophenylamino, 2-, 3- or 4-methylphenylamino, 3,5-dimethylphenylamino, 2-, 3- or 4-trifluoromethylphenylamino, 2-chloro-5-trifluoromethylphenylamino, 4-ethoxyphenylamino, 3,5-dichloro-4-methoxyphenylamino, 4-trifluoromethoxyphenylamino, 4-ethylthiophenylamino, 3-trifluoromethylthiophenylamino, 4-ethylsulphonylphenylamino, 3-trifluoromethylsulphonylphenylamino, 3,4-methylenedioxyphenylamino, 3,4-difluoromethylenedioxyphenylamino, 3,4-(tetrafluoroethylenedioxy)-phenylamino, 2,2,4,4-tetrafluorobenzodiox-1,3-ene-6-yl-amino; methoxycarbonylamino, ethoxycarbonylamino, butoxycarbonylamino and 2-ethylhexoxycarbonylamino, $R^4$ methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl, cylcohexyl, methoxy, ethoxy, n-propyloxy, n-butyloxy, sec.-butyloxy or n-pentyloxy, $R^5$ represents hydrogen, methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl or cyclohexyl or $R^4$ and $R^5$, together with the nitrogen atom, represent pyrrolidine, piperidine, 2-methylpiperidine, 3-methylpiperidine, 4-methylpiperidine, hexahydro-1H-azepine, morpholine, 2,6-dimethylmorpholine, thiazolidine, $N^1$-methylpiperazine or $N^1$-propylpiperazine.

In particular, compounds of the formula (I) may be mentioned in which $R^1$ represents methyl, ethyl, isopropyl, n-propyl, sec.-butyl, cyclopentyl or cyclohexyl, $R^2$ represents methyl, ethyl, isopropyl, tert.-butyl or phenyl, $R^3$ represents methanesulphonyl, chloromethanesulphonyl, chloroethanesulphonyl, p-toluylsulphonyl, benzoyl, 3-methyl-, 4-fluoro-, or 3-trifluoromethylbenzoyl; methylaminocarbonyl, N,N-dimethyl-, 2-methyl-2-cyanoethyl, 5-cyanopentyl-, 5-butoxycarbonylpentyl-, or 5-(2,2-dimethylpropoxycarbonyl)-pentylaminocarbonyl; 2-, 3- and 4-toluylaminocarbonyl; 3-trifluoromethyl- or 3-trifluoromethoxyphenyl-aminocarbonyl or 2-ethylhexoxycarbonyl-aminocarbonyl, $R^4$ represents methyl, methoxyethyl, methoxypropyl or cyanopentyl, and $R^5$ represents hydrogen, or $R^4$ and $R^5$ together represent butanylene, pentanylene or 3-oxapentanylene.

If, for example, 2-methoxycarbonyl-3-methyl-4-hydroxy-5-dimethylaminocarbonylthiophene and p-fluorobenzoyl chloride are used as starting materials, and pyridine is used as solvent and as hydrochloric acid acceptor for the preparation of the compounds of the formula (I), according to the invention by process version (a), or if methyl isocyanate is used according to process version (b), then the course of the reaction can be represented by the following equation:

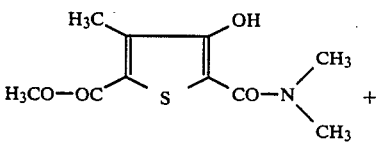

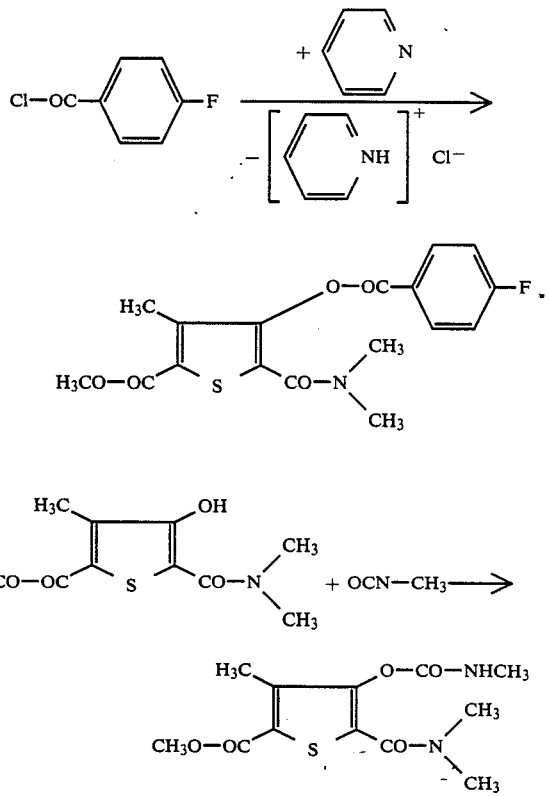

The sulphonic acid and carboxylic acid derivatives required as starting materials for carrying out the process (a) according to the invention are generally defined by the formula (III). Most of the compounds are known and can be prepared by known processes. The following should be particularly mentioned here: methane-, chloromethane-, 4-chlorobutane- and phenylsulphonyl chloride, 2-, 3- and 4-chlorophenylsulphonyl chloride, 3,4-dichloro-, 2-methyl-5-chloro-, 2- and 4-methylphenylsulphonyl chloride, 2-, 3- and 4-nitrophenylsulphonyl chloride, 2-chloro-5-nitrophenylsulphonyl chloride, 2,4,5-trifluoro-3-nitrophenylsulphonyl chloride, 2-methyl-5-nitrophenylsulphonyl chloride; acetyl bromide, isobutyroyl bromide, 2,2-dimethylpropanoyl chloride, trifluoroacetyl chloride, 4-bromobutyroyl chloride, 2,3-dibromo-propionyl chloride, methoxy- or butoxyacetyl chloride, ethylthioacetyl chloride, isopropyl-sulphonylacetyl chloride, 3-(methoxycarbonyl)propionyl chloride, methylthioethyloxyacetyl chloride, 2-phenylpropionyl chloride, 4-chlorophenylacetyl chloride, 2,4,5-trichlorophenoxyacetyl chloride, methacryloyl chloride, crotonoyl chloride, 2,3-dibromoacryloyl chloride, 3,4,4- or 4,4,4-trichlorocrotonoyl chloride, cinnamyl chloride, 4-chlorocinnamyl chloride, 3-(2-trifluoromethylphenyl)-acryloyl chloride, 3-(4-chlorophenyl)-3-chloroacryloyl chloride, propargyl chloride, cyclopropyl-, cyclopentyl- or cyclohexylcarbonyl chloride; methoxy-, isopropoxy-, 2-chloroethoxy-, 2,2,2-trifluoroethoxy-, 2,2,2-trichloroethoxy-, 2,3-tribromopropoxy- or 2-cyanoethoxycarbonyl chloride; benzoyl chloride, 2-, 3- or 4-chloro-, 3,4-dichloro-, 4-fluoro- and 3,5-dichloro-4-fluorobenzoyl chloride; 2-, 3- or 4l -toluyl chloride, 4-tert.-butyl-, 2-, 3- or 4-trifluoromethyl-, 2-methoxy-, 3,5-dimethoxy-, 2-methoxy-6-trifluoromethyl-, 4-ethylthio-, 4-ethylsulphinyl- or 4-ethylsulphonylbenzoyl chloride; 3- and 4-trifluoromethoxy-, 3-trifluoromethyl-4-isopropyl-, 3-chloro-4-trifluoromethoxy-, 4-chlorodifluoromethoxy-, 4-chlorodifluoromethylthio-, 4-trifluoromethylsulphinyl- or 4-trifluoromethylsulphonylbenzoyl halide; 2-, 3- or 4-pyridinecarbonyl chloride hydrochloride; N,N-dimethylamino-, N,N-dipropylamino-, N-methyl-N-phenylamino- or N-ethyl-N-phenylaminocarbonyl chloride; N-chlorocarbonyl-pyrrolidine, -piperidine, -3-methylpiperidine, -morpholine or -3,5-dimethyl-morpholine.

The isocyanates which are required as starting materials for carrying out the process according to the invention are generally defined by the formula (IV). Most of the compounds are known and can be prepared by known methods. The isocyanates can be prepared, for example, by reaction of the amino compounds with phosgene (Liebigs Ann. Chem. 562, 75–136, (1949)), by reaction of chlorocarbonyl isocyanate with alcohols or with amines (DOS (German Published Specification) 1,913,273), and by thermal cleavage of phenoxycarbonylamino compounds.

The following should be particularly mentioned here:

methyl isocyanate, butyl isocyanate, hexyl isocyanate, 2,2,2-trifluoroethyl isocyanate, 1-(trifluoromethyl)ethyl isocyanate, 6-chlorohexyl isocyanate, 2-cyanoethyl isocyanate, 1-cyano-1-methylethyl isocyanate, 1-cyano-1-methyl-propyl isocyanate, 1-cyano-1-ethyl-propyl isocyanate, 1-cyano-cyclopent-1-yl isocyanate, 1-cyano-cyclohex-1-yl isocyanate, 3-cyanopropyl isocyanate, 5-cyano-pentyl isocyanate, 6-cyanohexyl isocyanate, N-morpholinocarbonylmethyl isocyanate, 1-(N,N-diethylaminocarbonyl)ethyl isocyanate, N-pyrrolidino-carbonylethyl isocyanate, N-piperidino-carbonylpropyl isocyanate, N,N-dimethylaminocarbonylpentyl isocyanate, methoxycarbonylmethyl isocyanate, ethoxycarbonylmethyl isocyanate, butoxycarbonylethyl isocyanate, isobutoxycarbonylethyl isocyanate, 1-methoxycarbonyl-1-methyl-ethyl isocyanate, 1-propoxycarbonyl-1-methyl-ethyl isocyanate, 1-ethoxycarbonyl-1-ethyl-ethylisocyanate, 1-isobutoxycarbonyl-1-ethyl-ethyl isocyanate, methoxycarbonyl-propyl isocyanate, methoxycarbonyl-pentyl isocyanate, isopropoxycarbonyl-pentyl isocyanate, sec.-butyloxycarbonyl-pentyl isocyanate, allyloxycarbonyl-pentyl isocyanate, propargyloxycarbonyl-pentyl isocyanate, 2-ethoxycarbonyl-2-ethyl-butyl isocyanate, butoxycarbonylpentyl isocyanate, 2,2-dimethylpropyloxycarbonylpentyl isocyanate, methoxycarbonyl isocyanate, ethoxycarbonyl isocyanate, 2,2-dimethylpropyloxycarbonyl isocyanate, 2-ethylhexyloxycarbonyl isocyanate, octyloxycarbonyl isocyanate, phenyl isocyanate, 2-chlorophenyl isocyanate, 2,4,5-trichlorophenyl isocyanate, 4-fluorophenyl isocyanate, 2-, 3- or 4-methylphenyl isocyanate, 3,5-dimethylphenyl isocyanate, 2-, 3- or 4-trifluoromethylphenyl isocyanate, 2-chloro-5-trifluoromethylphenyl isocyanate, 4-ethoxyphenyl isocyanate, 3,5-dichloro-4-methoxyphenyl isocyanate, 4-trifluoromethoxyphenyl isocyanate, 4-ethoxythiophenyl isocyanate, 3-trifluoromethylthiophenyl isocyanate, 4-ethylsulphonylphenyl isocyanate, 3-trifluoromethylsulphonylphenyl isocyanate, 3,4-methylenedioxyphenyl isocyanate, 3,4-difluoromethylenedioxyphenyl isocyanate, 3,4-(tetrafluoroethylenedioxy)-phenyl isocyanate and 2,2,4,4-tetrafluorobenzodiox-1,3-ene-6-yl isocyanate.

Furthermore, 4-hydroxythiophene-5-carboxamides, which are generally defined by the formula (II), are required for the reactions to form the compounds according to the invention. These are subject to commonly assigned German Patent Application 3,523,313.3 filed June 29, 1985, corresponding to U.S. application Ser. No. 875,427, filed June 17, 1986, now pending and German Patent Application 3,602,889.4 filed Jan. 31, 1986. They are obtained by reacting 3-substituted 2,5-bis-(alkoxycarbonyl)-4-hydroxythiophenes of the general formula (VII)

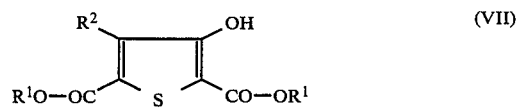

in which
R$^1$ and R$^2$ have the abovementioned meaning,
with amines of the formula (VIII)

in which
R$^4$ and R$^5$ have the abovementioned meaning,
if appropriate in the presence of a solvent or diluent and if appropriate in the presence of a tertiary organic base.

If, for example, 2,5-bis-(cyclopentyloxycarbonyl)-3-methyl-4-hydroxythiophene and 2-methoxyethylamine are used for the preparation of a starting compound of the formula (II), then the coarse of the reaction can be represented by the following equation:

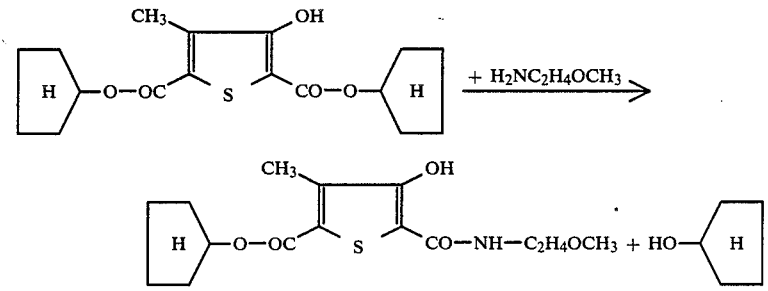

Examples of starting materials for the preparation of compounds of the formula (II) are, for example, 3-substituted 2,5-bis-(alkoxycarbonyl)-4-hydroxythiophenes such as methyl, ethyl, isopropyl, 1-methylpropyl, 2,2-dimethylpropyl, cyanomethyl, 2-cyanoethyl, 1-cyano-1-methylethyl, 2,2,2-trifluoroethyl, 2-methoxyethyl, 2-butylthioethyl, 2-ethylthioethyl, allyl, methallyl, propargyl, 1,1-dimethylpropargyl, cyclobutyl, cyclopentyl and cyclohexyl 3-methyl-4-hydroxy-thiophene-2,5-dicarboxylate; 2,2,2-trifluoro-ethyl 4-hydroxy-3-ethyl-, -3-propyl-, -3-isopropyl-, -3-butyl-, -3-tert.-butyl- and -3-phenylthiophene-2,5-dicarboxylate.

These are reacted with primary or secondary amines of the formula (VIII), such as methylamine, dimethylamine, ethylamine, diethylamine, n-propylamine, di-n-propylamine, iso-propylamine, sec.-butylamine, isobutylamine, n-butylamine, di-n-butylamine, amylamine, N-methylamylamine, 2-methoxyethylamine, 2-ethoxyethylamine, N-methyl-2-methoxyethylamine, 3-methoxypropylamine, 3-butoxypropylamine, 2-methylthioethylamine, 2-butylthioethylamine, N-methyl-3-butylthiopropylamine, 2-cyanoethylamine, 1-cyano-1-methylethylamine, 5-cyanopentylamine, 2,2-difluoroethylamine, 2,2,2-trifluoroethylamine, 3,3,3-trifluoropropylamine, 2,2-difluorobutylamine, 4,4,4-trifluorobutylamine, 1-trifluoromethylethylamine, allylamine, diallylamine, methallylamine, propargylamine, N-methylpropargylamine, cyclopropylamine, cyclobutylamine, cyclopentylamine, cyclohexylamine, N-methylcyclohexylamine, N-butoxyamine, N-methyl-N-butoxyamine, pyrrolidine, piperidine, 2-, 3- or 4-methylpiperidine, 2-ethylpiperidine, morpholine, 2,6-dimethylmorpholine, $N^1$-methylpiperazine, $N^1$-propylpiperazine, thiazolidine and hexahydro[1H]-azepine.

All organic solvents which are inert towards the reactants are suitable as diluents for the preparation of the 2-alkoxycarbonyl-substituted 4-hydroxythiophene-5-carboxamides of the formula (II); polar solvents are preferably used. The following examples should be mentioned here: acetonitrile, dimethylacetamide, dimethylformamide, dimethyl sulphoxide, N-methylpyrrolidone, dioxane, chlorobenzene, benzonitrile, ethyldiisopropylamine, triethylamine, tributylamine, dimethylcyclohexylamine, ethyldicyclohexylamine, dimethylbenzylamine, pyridine, picoline and quinoline, or the amine of the formula (VIII) to be reacted is used as solvent.

The reaction temperatures and the reaction duration are determined by the activity of the starting materials. In general, the reaction is carried out at temperatures between about 20° and 180° C., preferably between 40° and 150° C.

During the reaction of low-boiling amines, it can be advantageous to carry out the reaction under pressure.

Depending on the working conditions, the 2-alkoxycarbonyl-substituted 4-hydroxythiophene-5-carboxamides of the formula (II) precipitate in crystalline form, or they remain dissolved in the organic solvent and can be isolated by removal of the excess amine, which should be recovered to the greatest possible extent for economic reasons, by distillation and washing with water and dilute acid, the products being separated off from their solutions, if appropriate, by addition of non-polar solvents, such as cyclohexane, dibutyl ether or carbon tetrachloride.

All organic solvents which are inert towards the reactants are suitable as diluents for the reaction, according to the invention, of an alkoxycarbonyl-substituted 4-hydroxythiophene-carboxamide derivative of formula (II) with an acylating agent of the formula (III) according to process version (a); polar solvents are used preferably. Acetonitrile, acetone, chloroform, benzonitrile, dimethylacetamide, dimethylformamide, dimethyl sulphoxide, chlorobenzene, ethyl acetate, dioxane, methyl ethyl ketone, methylene chloride and tetrahydrofurane should be mentioned here as examples.

The reactions can also be carried out in heterogeneous systems, comprising water and a solvent which is not miscible with water.

Organic bases, preferably tertiary amines, are used as acid acceptors for the reaction. The following should be mentioned here: quinoline, dimethylbenzylamine, dimethylaniline, ethyldicyclohexylamine, ethyldiisopropylamine, picoline, pyridine and triethylamine.

Carbodiimides, such as, for example, dicyclohexylcarbodiimide, are preferably used as water-binding agents when carboxylic acids (formula III: X=OH) are used.

The reaction temperatures and the reaction duration are determined by the activity of the starting materials. In general, the reaction is carried out at temperatures between about $-50°$ and $+80°$ C., preferably between $-10°$ and 60° C.

Alternatively, to carry out the process according to the invention, the alkali metal or alkaline earth metal salts of the thiophene derivative to be reacted can be initially introduced in an inert solvent, or the salt is generated by adding alkali metal hydroxide solution, alcoholates or an appropriate alkaline earth metal compound to a mixture of the thiophene derivative and a high-boiling solvent, and then carefully dehydrating or removing the alcohol by distillation or adding an alkali metal or alkaline earth metal hydride to the mixture.

If the condensation of the hydroxythiophene derivative with a carboxylic acid is carried out by removal of water using a carbodiimide, for example dicyclohexylcarbodiimide, then the sparingly soluble urea produced can usually be separated off easily from the readily soluble compounds according to the invention.

All organic solvents which are inert towards the reactants are suitable as diluents for the reaction of alkoxycarbonyl-substituted 4-hydroxythiophene-carboxamides of the formula (II) with isocyanates of the formula (IV) according to process (b); polar solvents are used preferably. Acetonitrile, acetone, chloroform, benzonitrile, dimethylacetamide, dimethylformamide, dimethyl sulphoxide, chlorobenzene, ethyl acetate, dioxane, methyl ethyl ketone, methylene chloride and tetrahydrofurane should be mentioned here as examples.

Tertiary amines, such as triethylamine, triethylenediamine, pyridine, 4-dimethylaminopyridine or, alternatively, lead naphthenate and dibutyltin oxide can be used as catalysts for the reaction of the isocyanates with the hydroxythiophenes.

The reaction temperatures and the reaction duration are determined by the activity of the starting materials. In general, the reaction is carried out at temperatures between 20° and 120° C., preferably between 60° and 100° C.

It may be necessary to employ an excess of the isocyanate of the formula (IV) in the reaction.

For the reaction of an alkoxycarbonyl-substituted 4-hydroxythiophenecarboxamide derivative of the formula (II) firstly with phosgene and subsequently with an amine of the formula (VI) by process (c), a mixture comprising a 4-hydroxythiophene derivative of the formula (II), a tertiary amine, such as, for example, quinoline, dimethylbenzylamine, dimethylaniline, ethyldicyclohexylamine, ethyldiisopropylamine, picoline, pyridine or triethylamine, and an inert organic solvent, such as, for example, methylene chloride, chloroform, chlorobenzene, ethyl acetate, toluene or xylene, is added, in a first stage, to excess phosgene, dissolved in an inert organic solvent, the reaction being carried out, in general, between −50° and +80° C., preferably at 0° to +30° C.

After isolation of the 4-chlorocarbonyloxythiophene derivative of the formula (V), this is reacted with an amine of the formula (VI) or with a salt of the amine of the formula (VI), the acid produced being bound to a tertiary amine for economic reasons. If an amine salt is introduced into the reaction, twice the amount of tertiary amine must be employed. Suitable solvents for this reaction are, in principle, those which are miscible with water or nonmiscible, as listed above. In general, the reaction is carried out at temperatures corresponding to the phosgenation reaction.

Depending on the working conditions, the active compounds according to the invention precipitate in crystalline form, or they remain dissolved in the organic solvent and can then be separated off, after washing out the solvent with water, by careful concentration of the solution or by addition of non-polar organic solvents, such as cyclohexane, dibutyl ether, diisopropyl ether or carbontetrachloride. If appropriate, water-miscible polar solvents must be removed after the reaction by evaporation in vacuo.

If the compounds according to the invention are dissolved in a water-miscible solvent, then they can alternatively be precipitated by addition of water.

Some of the compounds according to the invention decompose at elevated temperature; in these cases, the melting points can only be determined with low accuracy or not at all. The presence of certain structural elements can also be seen from NMR spectra.

The active compounds according to the invention display a strong biological action and can be employed in practice for combating pests. The active compounds are thus suitable, inter alia, for use as plant-protecting agents, particularly as fungicides.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some causative organisms of fungal and bacterial diseases which come under the generic names listed above may be mentioned as examples, but not by way of limitation: Xanthomonas species, such as, for example, *Xanthomonas campestris* pv. oryzae; Pseudomonas species, such as, for example, *Pseudomonas syringae* pv. lachrymans; Erwinia species, such as, for example, *Erwinia amylovora;* Pythium species, such as, for example, *Pythium ultimum;* Phytophthora species, such as, for example, *Phytophthora infestans;* Pseudoperonospora species, such as, for example, *Pseudoperonospora humuli* or *Pseudoperonospora cubensis;* Plasmopara species, such as, for example, *Plasmopara viticola;* Peronospora species, such as, for example, *Peronospora pisi* or *P. brassicae;* Erysiphe species, such as, for example, *Erysiphe graminis;* Sphaerotheca species, such as, for example, *Sphaerotheca fuliginea;* Podosphaera species, such as, for example, *Podosphaera leucotricha;* Venturia species, such as, for example, *Venturia inaequalis;* Pyrenophora species, such as, for example, *Pyrenophora teres* or *P. graminea* (conidia form: Drechslera, syn: Helminthosporium); Cochliobolus species, such as, for example, *Cochliobolus sativus* (conidia form: Drechslera, syn: Helminthosporium); Uromyces species, such as, for example, *Uromyces appendiculatus;* Puccinia species, such as, for example, *Puccinia recondita;* Tilletia species, such as, for example, *Tilletia caries;* Ustilago species, such as, for example, *Ustilago nuda* or *Ustilago avenae;* Pellicularia species, such as, for example, *Pellicularia sasakii;* Pyricularia species, such as, for example, *Pyricularia oryzae;* Fusarium species, such as, for example, Fusarium culmorum; Botrytis species, such as, for example, *Botrytis cinerea;* Septoria species, such as, for example, *Septoria nodorum;* Leptosphaeria species, such as, for example, *Leptosphaeria nodorum;* Cercospora species, such as, for example, *Cercospora canescens;* Alternaria species, such as, for example, *Alternaria brassicae* and Pseudocercosporella species, such as, for example, *Pseudocercosporella herpotrichoides.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, as well as ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

The compounds of the formula (I) according to the invention are particularly effective against fungal diseases in rice, but they also show good effectiveness, at the appropriate applicational concentrations, against Oomyceten, the pathogens of apple scab and against Botrytis pathogens.

Some of the active compounds are suitable for combating animal pests, such as insects and arachnida, particularly insects, which are encountered in agriculture, in forestry, in the protection of stored products and of materials, and in the hygiene field, and have good plant tolerance and favorable toxicity to warm-blooded animals. The abovementioned pests include:

From the order of the Isopoda, for example, *Oniscus asellus, Armadillidium vulgare* and *Porcellio scaber*. From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermoptera, for example, *Foricula auricularia*. From the order of the Isoptera, for example, Reticulitermes spp.. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci.* From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma Lanigerum, Hyalopterus arundinis, Macrosiphum avenae,* Myzus spp. *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Spodoptera exigua, Mamestra brassicae, Panolis flammea, Prodenia litura,* Spodoptera spp., Trichoplusiani, *Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homonamagnanima* and *Tortrix viridana.*

From the order of the Coleoptera, for example, *Anobium punctatum, Rhizopertha dominica, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro, Argas* spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa, Panonychus* spp. and *Tetranychus* spp.

The active compounds according to the invention can be present in their commercially available formulations and in the use forms, prepared from these formulations, as a mixture with other active compounds, such as insecticides, baits, sterilizing agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compounds are distinguished by an excellent residual action on wood and clay as well as a good stability to alkali on limed substrates.

PREPARATION EXAMPLES

Example 1

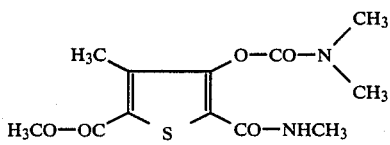

5.9 g of dimethylcarboxamide chloride are added dropwise to a suspension comprising 10 g of 2-methoxycarbonyl-3-methyl-4-hydroxythiophene-5-methylcarboxamide, 40 ml of pyridine and 10 mg of dimethylaminopyridine. The mixture is stirred for 2 h at 45° C. and 21 h at 22° C. The precipitated crystalline substance is separated off, washed with water until free of chloride, and dried at 60° C./0.1 mbar. 6.9 g of 2-methoxycarbonyl-3-methyl-4-(dimethylaminocarbonyloxy)-thiophene-5-methylcarboxamide having a melting point of 173° C. are obtained. A further product fraction of 3.2 g can be obtained from the mother liquor.

Preparation of the precursor

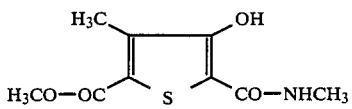

20 g of 2,5-bis-(methoxycarbonyl)-3-methyl-4-hydroxythiophene are dissolved in 110 ml of dimethylformamide. Methylamine is passed in. The methylamine salt of 4-hydroxythiophene derivate, which is insoluble, is produced initially. The mixture is heated, while continuing to pass in methylamine, for 5 h at 60° C. and 3 h at 80° C. The mixture is evaporated in vacuo. The evaporation residue is treated with 300 ml of ethylacetate and 100 ml of ice-cold 5% strength sulphuric acid. The crystals produced are separated off, washed with water and dried at 60° C./0.1 mbar.

Yield: 11.6 g of 2-methoxycarbonyl-3-methyl-4-hydroxythiophene-5-methylcarboxamide having a melting point of 188° C. (decomposition).

Example 2

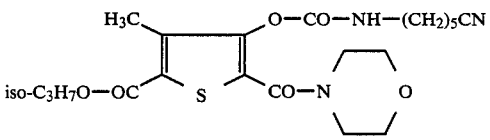

9 g of 2-(isopropoxycarbonyl)-3-methyl-4-hydroxythiophene-5-carboxymorpholide, 5 ml of acetonitrile, 5 g of 5-cyanopentyl isocyanate and 100 mg of triethylenediamine are maintained at 100° C. for 15 h. The reaction mixture is diluted with 50 ml of toluene, treated with 1 g of silica gel, and evaporated in vacuo. The evaporation residue is dried at 60° C./0.1 mbar. After treatment with diisopropyl ether, the product crystallizes. The crystals are separated off, washed with diisopropyl ether and dried at 60° C./0.1 mbar.

Yield: 12.1 g of 2-(isopropoxycarbonyl)-3-methyl-4-(5-cyanopentylaminocarbonyloxy)-thiophene-5-carboxymorpholide having a melting point of 81° C.

Preparation of the precursor

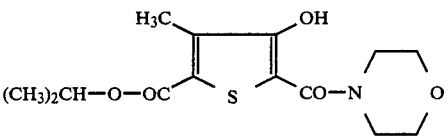

90 g of 2,5-bis-(isopropoxycarbonyl)-3-methyl-4-hydroxythiophene and 450 g of morpholine are heated for 9½ h at 124° C. The excess morpholine is evaporated off in vacuo. The evaporation residue is dissolved in 600 ml of dichloromethane, and washed twice with ice-cold, dilute sulphuric acid and once with water. The solution is dried using sodium sulphate. After evaporation off of the solvent, the residue is titrated with a little diisopropyl ether, separated off and dried at 60° C./0.1 mbar.

Yield: 78.9 g of 2-isopropoxycarbonyl-3-methyl-4-hydroxy-5-(1-aza-4-oxacylohex-1-ylcarbonyl)-thiophene having a melting point of 123° C.

The compounds of the formula (I) are obtained in the same fashion:

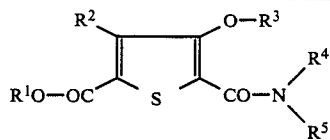

| Ex-No. | Prep. acc. to Ex. | R¹ | R² | R³ | R⁴ | R⁵ | Physical data [M = melting point °C.] |
|---|---|---|---|---|---|---|---|
| 3 | 2 | H₃C— | H₃C— | —OC—NH(CH₂)₅CN | —CH₃ | —H | M 128-146 crude product |
| 4 | 2 | H₃C— | (CH₃)₂CH— | —OC—NH—C₆H₄—CH₃(m) | —C₂H₄—O—C₂H₄— | | M 154 from acetonitrile |
| 5 | 2 | H₅C₂— | H₃C | —OC—NH—CH₃ | —(CH₂)₅— | | M 118 from diisopropyl ether |
| 6 | 1 | H₅C₂ | H₃C— | —OC—N(CH₃)₂ | —(CH₂)₅— | | viscous |
| 7 | 2 | n-H₇C₃— | H₃C— | —OC—NH—C₆H₄—CF₃(m) | —(CH₂)₅— | | |
| 8 | 2 | n-H₇C₃— | H₃C— | —OC—NH—C₆H₄—CH₃(m) | —(CH₂)₅— | | M 134 from acetonitrile |
| 9 | 2 | (CH₃)₂CH— | H₃C— | —OC—NH—C₆H₄—OCF₃(m) | —C₂H₄—O—C₂H₄— | | M 165 from acetonitrile |
| 10 | 1 | " | " | —SO₂—CH₂Cl | —(CH₂)₅— | | M 85 from petroleum ether |
| 11 | 2 | " | " | —OC—NH—C₆H₄—CH₃(m) | —(CH₂)₄— | | M 124 from acetonitrile |
| 12 | 1 | " | " | —OC—C₆H₄—CH₃(m) | —(CH₂)₅—CN | —H | M 79 from diisopropyl ether |
| 13 | 1 | " | " | —OC—C₆H₄—CH₃(m) | —C₂H₄—O—C₂H₄— | | M 124 from petroleum ether |
| 14 | 2 | " | " | —OC—NH—CH₃ | —C₂H₄—O—C₂H₄— | | M 130 from diisopropyl ether |
| 15 | 2 | " | " | —OC—NH—CH₃ | —(CH₂)₅— | | M 142 from acetonitrile |
| 16 | 2 | " | " | —OC—NH—(CH₂)₅—CN | —(CH₂)₅— | | M 78 from acetonitrile |
| 17 | 1 | " | " | —OC—N(CH₃)₂ | —C₂H₄—O—C₂H₄— | | M 112 from diisopropyl ether |
| 18 | 2 | (H₃C)₂CH— | H₃C— | —OC—NH—C₆H₄—CF₃(m) | —C₂H₄—O—C₂H₄— | | M 165 from acetonitrile |
| 19 | 2 | " | " | —OC—NH—(CH₂)₅—COOC₄H₉ | —C₂H₄—O—C₂H₄— | | M 81 from ligroin |
| 20 | 2 | " | " | —OC—NH—(CH₂)₅—COOCH₂C(CH₃)₃ | —C₂H₄—O—C₂H₄— | | M 57 from petroleum ether |
| 21 | 2 | " | " | —OC—NH—C₆H₄—CH₃(m) | —CH₂)₅— | | viscous |
| 22 | 1 | " | C₆H₅— | —OC—C₆H₅ | —C₂H₄—O—C₂H₄— | | M 131 from toluene/ diisopropyl ether |
| 23 | 2 | H₅C₂(H₃C)CH— | H₃C | —OC—NH(CH₂)₅—CN | —C₂H₄—O—C₂H₄— | | viscous |
| 24 | 2 | " | " | —OC—NH—C₆H₅—CH₃(m) | —CH₂)₅— | | M 150 from diethyl ketone |
| 25 | 2 | " | " | —OC—NH—C₆H₄—CF₃(m) | —(CH₂)₅— | | M 141 from diethyl ketone |
| 26 | 2 | " | " | —OC—NH—C₆H₄—Cl (p) | —(CH₂)₅— | | M 157 from acetone |
| 27 | 2 | " | " | —OC—NH—(CH₂)₅—CN | —(CH₂)₅— | | viscous |
| 28 | 2 | " | " | —OC—NH—C₆H₄—CH₃(o) | —C₂H₄—O—C₂H₄— | | M 114 from diisopropyl ether |
| 29 | 2 | H₃C— | H₃C— | —OC—NH—CH₃ | —CH₃ | —H | M decomposition >100° |
| 30 | 1 | H₃C— | H₃C— | —OC—C₆H₄—F(p) | —CH₃ | —H | M 187 from diethyl ketone |
| 31 | 2 | H₅C₂(H₃C)CH— | H₃C— | —OC—NH—C₆H₄—CF₃(m) | —C₂H₄—O—C₂H₄— | | M >153° from acetonitrile |
| 32 | 2 | H₅C₂— | H₃C— | —OC—NH—C₆H₄—CH₃(o) | —C₂H₄—O—C₂H₄— | | M 116° from acetonitrile |
| 33 | 2 | (H₃C)₂CH | H₃C— | —OC—NH—C₆H₄—CF₃(m) | —C₅H₁₀— | | M 156° from acetonitrile |
| 34 | 2 | H₇C₃ | H₃C— | —OC—NH—C₆H₄—CH₃(m) | —C₂H₄—O—C₂H₄— | | M 148,5° from acetonitrile |
| 35 | 2 | H₇C₃ | H₃C— | —OC—NH—C₆H₄—CF₃(m) | —C₂H₄—O—C₂H₄— | | M 137° from acetonitrile |

Use example

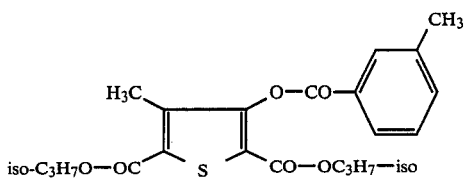

Example

Pyricularia test (rice)/protective
Solvent: 12.5 parts of acetone
Emulsifier: 0.3 parts of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of Pyricularia oryzae. The plants are then placed in a greenhouse at 100% relative atmospheric humidity and 25° C.

Evaluation of the disease infestation is carried out 4 days after the inoculation.

In this test, the compounds according to preparation examples: 2, 16, 23 and 20, for example, show clearly superior effectiveness compared to the prior art.

It is understood that the specification and examples are illustrative but not limitative of the present invention and that other embodiments within the spirit and scope of the invention will suggest themselves to those skilled in the art.

We claim:

1. An acyloxythiophene-carboxyamide of the formula

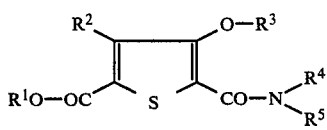

in which
$R^1$ represents alkyl, alkoxyalkyl, alkylthioalkyl, fluoroalkyl, cyanoalkyl, alkenyl, alkinyl or cycloalkyl,
$R^2$ represents alkyl or optionally substituted phenyl,
$R^3$ represents the —OC—Q radical, in which
Q represents alkyl which is optionally identically or differently substituted by halogen, alkoxy, alkylthio, alkylsulphonyl, alkylthioalkoxy, alkoxycarbonyl, phenyl, phenoxy or halogenophenoxy; alkenyl which is optionally identically or differently substituted by halogen, phenyl, halogenophenyl or halogenoalkylphenyl; alkinyl; cycloalkyl; alkoxy which is optionally substituted by halogen or cyano; phenyl which is optionally identically or differently substituted by halogen, alkyl, halogenoalkyl, alkoxy, halogenoalkoxy, alkylthio, halogenoalkylthio, alkylsulphinyl, halogenoalkylsulphinyl, alkylsulphonyl or halogenoalkylsulphonyl;
$R^4$ represents alkyl, alkoxyalkyl, alkylthioalkyl, cyanoalkyl, fluoroalkyl, alkenyl, alkinyl, cycloalkyl or alkoxy,
$R^5$ represents hydrogen, alkyl, alkoxyalkyl, alkylthioalkyl, fluoroalkyl, cyanoalkyl, alkenyl, alkinyl or cycloalkyl.

2. An acyloxythiophene-carboxamide according to claim 1, in which
$R^1$ represents alkyl having 1 to 5 carbon atoms, alkoxyalkyl, or alkylthioalkyl having 1 to 5 carbon atoms in each of the alkyl parts, fluoroalkyl having 1 to 5 carbon atoms and 1 to 5 fluorine atoms, cyanoalkyl having 1 to 5 carbon atoms in the alkyl part, alkenyl having 3 or 4 carbon atoms, alkinyl having 3 to 5 carbon atoms, or cycloalkyl having 4 to 6 carbon atoms,
$R^2$ represents alkyl having 1 to 4 carbon atoms, or optionally mono- to pentasubstituted phenyl, the substituents being identical or different and being alkyl having 1 to 4 carbon atoms, alkoxy or alkylthio each having 1 to 4 carbon atoms, halogen, nitro, halogenoalkyl, halogenoalkoxy or halogenoalkylthio each having 1 to 4 carbon atoms and 1 to 5 identical or different halogen atoms,
$R^3$ represents the radical —OC—Q, in which
Q represents alkyl having 1 to 4 carbon atoms and which can be optionally substituted by up to 4 identical or different halogen atoms, alkoxy, alkylthio, alkylsulphonyl or alkoxycarbonyl each having up to 4 carbon atoms, alkylthioalkoxy having up to 2 carbon atoms in each alkyl unit, phenyl, phenoxy, or halogenophenoxy having up to 3 identical or different halogen atoms; alkenyl having 2 to 4 carbon atoms and which can be substituted by 1 to 4 identical or different halogen atoms, phenyl, halogenophenyl having 1 to 3 identical or different halogen atoms or halogenoalkylphenyl having 1 to 3 identical or different halogen atoms and 1 or 2 carbon atoms in the halogenoalkyl radical; alkinyl having up to 3 carbon atoms; cycloalkyl having 3 to 6 carbon atoms; alkoxy, having 1 to 4 carbon atoms, which can be optionally substituted by up to 3 identical or different halogen atoms, or cyano; phenyl which can be optionally mono- to trisubstituted, identically or differently, by identical or different halogen atoms, alkyl having 1 to 4 carbon atoms, halogenoalkyl having 1 or 2 carbon atoms and 1 to 3 identical or different halogen atoms, alkoxy having 1 to 2 carbon atoms, halogenoalkoxy having 1 or 2 carbon atoms and 1 to 3 identical or different halogen atoms, alkylthio having 1 or 2 carbon atoms, halogenoalkylthio having 1 or 2 carbon atoms and 1 to 3 identical or different halogen atoms, alkylsulphinyl having 1 or 2 carbon atoms, halogenoalkylsulphinyl having 1 or 2 carbon atoms and 1 to 3 identical or different halogen atoms, alkylsulphonyl having 1 or 2 carbon atoms, or halogenoalkylsulphonyl having 1 or 2 carbon atoms and 1 to 3 identical or different halogen atoms;
$R^4$ represents alkyl having 1 to 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl each having 3 to 5 carbon atoms, cycloalkyl having 3 to 6 carbon atoms, or alkoxy having 1 to 5 carbon atoms, $R^5$ represents hydrogen, alkyl having 1 to 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl having 3 to 5 carbon atoms, or cycloalkyl having 6 carbon atoms, or 3. An acyloxythiophene-carboxamide according to claim 1, in which $R^1$ represents methyl, ethyl, n- or iso-propyl, 2,2-dimethylpropyl, 2-methoxyethyl, 2-ethoxyethyl, 2-methylthioethyl, 2-ethylthioethyl, 2,2,2-trifluoroethyl, cyanomethyl, cyanoethyl, allyl, methallyl, 2-propinyl, 1,1-dimethyl-2-propinyl, cyclopentyl or cyclohexyl, $R^2$ represents methyl, ethyl, n-propyl, isopropyl, n-butyl, sec,-butyl, iso-butyl or tert.-butyl, phenyl or phenyl which is mono- to trisubstituted, identically or differently, by halogen, $R^3$ represents the —OC—Q radical, where represents methyl, ethyl, isopropyl, butyl, dichloromethyl, trichloromethyl, trifluoromethyl, 1-bromo-1-methylethyl, methoxymethyl, butoxymethyl, 2-butylthioethyl, propylsulphonylmethyl, methoxycarbonylethyl, butoxycarbonylethyl, methylthioethoxymethyl, benzyl, phenoxymethyl, 1-phenoxyethyl, 1-(4-chlorophenoxy)-ethyl, 2,4-dichloro-phenoxymethyl; vinyl, propen-1-yl, 2-chlorovinyl, 2-(phenyl)-vinyl, 2-(4-chlorophenyl)-vinyl, 2-(4-chlorophenyl)-2-chlorovinyl, 2-(2-trifluoro-methylphenyl)vinyl, ethinyl, 2-methylethinyl, cyclopropyl, cyclobutyl, cyclopentyl, cyclohexyl, methoxy, isopropoxy, butoxy, 2-chloroethoxy, 2,2,2-trichloroethoxy, 2,2,2-trifluoroethoxy, 2-cyanoethoxy; phenyl, 2-, 3- or 4-chlorophenyl, 2-bromophenyl, 4-fluorophenyl, 2-, 3- or 4-methylphenyl, 4-tert.butylphenyl, 2-, 3- or 4-trifluoromethyl-phenyl, 3-chloro-4-trifluoromethylphenyl, 4-methoxyphenyl, 3-trifluoromethoxyphenyl, 3-chloro-4-trifluoromethoxyphenyl, 4-chlorodifluoromethoxyphenyl, 4-ethylthiophenyl, 4-trifluoromethylthiophenyl, 4-ethylsulphinylphenyl, 4-trifluoromethylsulphinylphenyl, 4-methylsulphonylphenyl, 4-trifluoromethyl-sulphonylphenyl;

$R^4$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl, cyclohexyl, methoxy, ethoxy, n-propyloxy, n-butyloxy, sec.butyloxy or n-pentyloxy, $R^5$ represents hydrogen, methyl, ethyl, n- or isopropyl, 2,2-dimethylpropyl, 2-methoxy-ethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl or cyclohexyl.

4. An acyloxythiophene-carboxamide according to claim 1, in which $R^1$ represents methyl, ethyl, isopropyl, n-propyl, sec.-butyl, cyclopentyl or cyclohexyl, $R^2$ represents methyl, ethyl, isopropyl, tert.-butyl or phenyl, $R^3$ represents 3-trifluoromethylbenzoyl; methylaminocarbonyl, N,N-dimethyl-, 2-methyl-2-cyanoethyl, 5-cyanopentyl-, 5-butoxycarbonylpentyl-, or 5-(2,2-dimethylpropoxycarbonyl)-pentylaminocarbonyl; 2-, 3- and 4-toluylaminocarbonyl; 3-trifluoromethyl- or 3-trifluoromethoxyphenyl-aminocarbonyl or 2-ethylhexoxycarbonyl-aminocarbonyl, $R^4$ represents methyl, methoxyethyl, methoxypropyl or cyanopentyl, and $R^5$ represents hydrogen.

5. An acyloxythiophene-carboxamide according to claim 1, wherein such compound is 2-methoxycarbonyl-3-methyl-4-(4-fluorobenzoyloxy)-thiophene-5-methyl-carboxamide of the formula

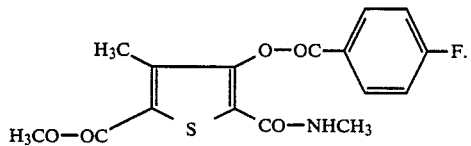

6. A fungicidal composition comprising a fungicidally effective amount of a compound according to claim 1 and a diluent.

7. A method of combating fungi which comprises applying to fungi or to a fungus habitat a fungicidally effective amount of a compound according to claim 1.

8. The method according to claim 7, wherein such compound is 2-methoxycarbonyl-3-methyl-4-(4-fluorobenzoyloxy)-thiophene-5-methylcarboxamide.

9. An acyloxythiophene-carboxamide of the formula

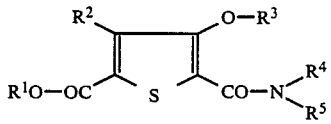

in which $R^1$ represents alkyl, alkoxyalkyl, alkylthioalkyl, fluoroalkyl, cyanoalkyl, alkenyl, alkinyl or cycloalkyl, $R^2$ represents alkyl or optionally substituted phenyl, $R^3$ represents alkylsulphonyl, halogenoalkylsulphonyl, or optionally substituted phenylsulphonyl, $R^4$ represents alkyl, alkoxyalkyl, alkylthioalkyl, cyanoalkyl, fluoroalkyl, alkenyl, alkinyl, cycloalkyl or alkoxy, $R^5$ represents hydrogen, alkyl, alkoxyalkyl, alkylthioalkyl, fluoroalkyl, cyanoalkyl, alkenyl, alkinyl or cycloalkyl.

10. An acyloxythiophene-carboxamide according to claim 9, in which $R^1$ represents alkyl having 1 to 5 carbon atoms, alkoxyalkyl, or alkylthioalkyl having 1 to 5 carbon atoms in each of the alkyl parts, fluoroalkyl having 1 to 5 carbon atoms and 1 to 5 fluorine atoms, cyanoalkyl having 1 to 5 carbon atoms in the alkyl part, alkenyl having 3 or 4 carbon atoms, alkinyl having 3 to 5 carbon atoms, or cycloalkyl having 4 to 6 carbon atoms, $R^2$ represents alkyl having 1 to 4 carbon atoms, or optionally mono- to pentasubstituted phenyl, the substituents being identical or different and being alkyl having 1 to 4 carbon atoms, alkoxy or alkylthio each having 1 to 4 carbon atoms, halogen, nitro, halogenoalkyl, halogenoalkoxy or halogenoalkylthio each having 1 to 4 carbon atoms and 1 to 5 identical or different halogen atoms, $R^3$ represents alkylsulphonyl having 1 to 4 carbon atoms, halogenoalkylsulphonyl having 1 to 4 carbon atoms and 1 to 4 identical or different halogen atoms, or phenylsulphonyl, where the phenyl radical can be mono- to pentasubstituted, identically or differently, by halogen, alkyl having 1 to 4 carbon atoms or by nitro, $R^4$ represents alkyl having 1 to 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl each having 3 to 5 carbon atoms, cycloalkyl having 3 to 6 carbon atoms, or alkoxy having 1 to 5 carbon atoms, $R^5$ represents hydrogen, alkyl having 1 to 5 carbon atoms, alkoxyalkyl or alkylthioalkyl each having 1 to 5 carbon atoms in each alkyl part, cyanoalkyl having 1 to 5 carbon atoms in the alkyl part, fluoroalkyl having 1 to 3 fluorine atoms and 1 to 5 carbon atoms, alkenyl or alkinyl having 3 to 5 carbon atoms, or cycloalkyl having 6 carbon atoms.

11. An acyloxythiophene-carboxamide according to claim 9, in which $R^1$ represents methyl, ethyl, n- or iso-propyl, 2,2-dimethylpropyl, 2-methoxyethyl, 2-ethoxyethyl, 2-methylthioethyl, 2-ethylthioethyl, 2,2,2-trifluoroethyl, cyanomethyl, cyanoethyl, allyl, methallyl, 2-propinyl, 1,1-dimethyl-2-propinyl, cyclopentyl or cyclohexyl, $R^2$ represents methyl, ethyl, n-propyl, iso-propyl, n-butyl, sec,-butyl, iso-butyl or tert.-butyl, phenyl or phenyl which is mono- to trisubstituted, identically or differently, by halogen, $R^3$ represents methanesulphonyl, chloromethanesulphonyl, phenylsulphonyl, 2-, 3- and 4-chlorophenylsulphonyl, 3,4-dichlorophenylsulphonyl, 2- and 4-methylphenylsulphonyl, 3-chloro-4-methylphenylsulphonyl, 2-, 3- and 4-nitrophenylsulphonyl, 2-chloro-5-nitrophenylsulphonyl, 2,4,5-trifluoro-3-nitrophenylsulphonyl or 2-methyl-5-nitrophenylsulphonyl, $R^4$ represents methyl, ethyl, n- or iso-propyl, 2,2-dimethylpropyl, 2-methoxyethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl, cyclopropyl, cyclobutyl, cyclopentyl, cyclohexyl, methoxy, ethoxy, n-propyloxy, n-butyloxy, sec.-butyloxy or n-pentyloxy, $R^5$ represents hydrogen, methyl, ethyl, n- or iso-propyl, 2,2-dimethylpropyl, 2-methoxy-ethyl, 2-ethoxyethyl, 2-propoxyethyl, 3-methoxypropyl, 3-ethoxypropyl, 3-butoxypropyl, 2-methylthioethyl, 2-ethylthioethyl, 2,2,2-trifluoroethyl, 2-cyanoethyl, 1-methyl-1-cyanoethyl, ω-cyanopentyl, allyl, methallyl, 2-propinyl, 1,1-dimethyl-2-propinyl or cyclohexyl.

12. An acyloxythiophene-carboxamide according to claim 9, in which $R^1$ represents methyl, ethyl, isopropyl, n-propyl, sec.-butyl, cyclopentyl or cyclohexyl, $R^2$ represents methyl, ethyl, isopropyl, tert.-butyl or phenyl, $R^3$ represents methanesulphonyl, chloromethanesulphonyl, chloroethanesulphonyl, p-toluylsulphonyl, benzoyl or 3-methyl-, 4-fluoro-, or 3-trifluoromethylbenzoyl, $R^4$ represents methyl, methoxyethyl, methoxypropyl or cyanopentyl, and $R^5$ represents hydrogen.

13. A fungicidal composition comprising a fungicidally effective amount of a compound according to claim 9 and a diluent.

14. A method of combating fungi which comprises applying to fungi or to a fungus habitat a fungicidally effective amount of a compound according to claim 9.

* * * * *

UNITED STATES PATENT AND TRADEMARK OFFICE
CERTIFICATE OF CORRECTION

PATENT NO. : 4,863,954

DATED : September 5, 1989

INVENTOR(S) : Werner Daum, et al

It is certified that error appears in the above-identified patent and that said Letters Patent is hereby corrected as shown below:

Col. 23, line 21     Before "represents" insert --Q--

Col. 26, line 15     Before "$R^5$" delete "-pl" and start new paragraph

Signed and Sealed this

Twelfth Day of March, 1991

Attest:

HARRY F. MANBECK, JR.

*Attesting Officer*     *Commissioner of Patents and Trademarks*